(12) United States Patent
McGowan et al.

(10) Patent No.: US 6,238,627 B1
(45) Date of Patent: May 29, 2001

(54) REACTION BLOCK AND COVER

(75) Inventors: David Craig McGowan, Arlington; Erik T. Mankarios, Needham; Edward M. Manley, Medford; Christopher C. Werner, Bellingham, all of MA (US)

(73) Assignee: ArQule, Inc., Medford, MA (US)

( * ) Notice: Subject to any disclaimer, the term of this patent is extended or adjusted under 35 U.S.C. 154(b) by 0 days.

(21) Appl. No.: 09/140,145

(22) Filed: Aug. 26, 1998

(51) Int. Cl.[7] ....................................... B01J 19/00
(52) U.S. Cl. .................. 422/130; 422/99; 422/101; 422/129; 422/131; 422/138
(58) Field of Search ................ 422/99, 100, 101, 422/129, 130, 131, 138

(56) References Cited

U.S. PATENT DOCUMENTS

| | | |
|---|---|---|
| 639,980 | 12/1899 | Hickey . |
| 951,110 | 3/1910 | Gilchrist . |
| 1,916,690 | 7/1933 | Schnetzler . |
| 2,328,029 | 8/1943 | Porter . |
| 4,625,096 | 11/1986 | Fletcher . |
| 5,035,774 | 7/1991 | Rabren . |
| 5,160,413 | 11/1992 | Allison . |
| 5,219,528 | 6/1993 | Clark . |
| 5,324,483 | * 6/1994 | Cody et al. ............ 422/131 |
| 5,398,806 | 3/1995 | Quinn . |
| 5,472,672 | 12/1995 | Brennan . |
| 5,609,826 | 3/1997 | Cargill et al. . |
| 5,753,187 | 5/1998 | Reynolds et al. . |

* cited by examiner

Primary Examiner—T. Tung
Assistant Examiner—Dwayne K. Handy
(74) Attorney, Agent, or Firm—Fish & Richardson P.C.

(57) ABSTRACT

A cover assembly of the type disposed over a reaction block for preparing reaction mixtures and, in particular, for enabling reflux condensation of the mixtures is provided. The cover assembly includes a cover assembly having a cover housing with a gas inlet adapted to receive a cooling gas from an external source and an internal cavity through which the reaction vials extend. The cover assembly also includes at least one gas port in communication with the internal cavity and through which the cooling gas from the gas inlet flows to cool portions of the reaction vials which are distal their lower ends.

27 Claims, 7 Drawing Sheets

REACTION BLOCK AND COVER

FIELD OF THE INVENTION

This invention relates to a reaction block and cover to prepare reaction mixtures.

BACKGROUND OF THE INVENTION

In recent years, methods for simultaneously preparing large numbers of chemical compounds have attracted increasing interest. One approach for preparing the compounds is to arrange individual reaction vials within a single reaction unit or block.

A reaction block generally includes a large number of reaction vials, each of which corresponds to a reaction vial for containing a reaction mixture. The reaction block provides a spatially-addressable approach for analyzing the synthesis of a family or library of chemical compounds. Using reaction blocks in this way allows larger number of compounds to be generated and screened more quickly. Thus, reaction blocks are valuable in reducing, for example, the time necessary in bringing new pharmaceutical drugs to market.

Although different reaction blocks are known in which the temperature of the block, and thus the reaction mixture within the vessel, can be controlled, it is difficult to carry out a reflux reaction in a simple, reliable way using known reaction blocks.

SUMMARY OF THE INVENTION

The invention is based on the discovery that a cover assembly that directs a stream of cooling gas (e.g., air) to the middle or upper ends of reaction vials nested in a reaction block is effective to cool the vials sufficiently to carry out a reflux reaction without the need for cooling the ambient air around the reaction block and without the need for a sophisticated and possibly complex cooling system.

In one aspect, the cover assembly includes a cover housing having a gas inlet adapted to receive a cooling gas from an external source and an internal cavity into which the reaction vials extend during operation. The cover assembly also includes an inlet port, positioned between the gas inlet and the internal cavity, through which the cooling gas from the gas inlet flows to cool upper ends of the reaction vials; a movable vane disposed within the internal cavity and configured to be positioned and secured over a portion of the inlet port; and an outlet configured to allow the cooling gas to exit the internal cavity after cooling the upper ends of the reaction vials.

In another aspect, the cover assembly includes a cover housing having a gas inlet adapted to receive a cooling gas from an external source; an internal cavity into which the reaction vials extend; and a plurality of inlet ports, positioned between the gas inlet and the internal cavity and through which the cooling gas from the gas inlet flows to cool upper ends of the reaction vials. The cover assembly also includes an outlet configured to allow the cooling gas to exit the internal cavity after cooling upper ends of the reaction vials.

In still another aspect, the cover assembly includes a gas inlet adapted to receive a cooling gas from an external source; a top wall and a plurality of sidewalls which together define an internal cavity adapted to receive upper ends of each reaction vial during operation; and a plurality of outlet ports formed within at least one of the sidewalls to allow the cooling gas to exit the internal cavity after cooling the upper ends of each reaction vial.

Embodiments of these aspects of the invention may include one or more of the following features.

The cover housing defines a plenum chamber positioned between the gas inlet and the inlet port (or plurality of inlet ports); a plenum member having the inlet port formed therein, an upper surface, and a bottom surface; and a top cover disposed over the plenum member and having a bottom surface which together with the upper surface of the plenum member define the plenum chamber. The gas inlet can be provided within the top cover. The cover assembly can also include a spacer positioned between the plenum member and the reaction block. The spacer has an upper surface which together with the bottom surface of the plenum member defines the internal cavity and the gas outlet.

In other aspects of the invention, a reaction block includes one of the above described cover assemblies and further includes a base including an array of first holes formed therein. Each of the first holes are sized and configured to receive a lower end of a reaction vial. With this arrangement, the array of holes defines a pattern of rows and columns so that the upper ends of the reaction vials themselves form channels to allow the cooling gas to exit the cover through exit openings positioned at an end of the cover assembly and between adjacent rows or columns of the reaction vials.

In embodiments of these reaction blocks, the spacer can include an array of second holes located in a pattern corresponding to the array of first holes. The array of first holes defines a pattern of rows and columns. The base is formed of a first material having a first thermal conductivity characteristic and the spacer is formed of a thermally insulative material having a second thermal conductivity characteristic less than the first thermal conductivity characteristic. In essence, the spacer serves as a thermal isolating barrier between the upper and lower ends of the reaction vials, thereby enhancing reflux condensation. A thermal conductivity characteristic (or coefficient of conductivity) is a measure of the time rate of transfer of heat by conduction through a unit thickness across a unit area for a unit difference of temperature.

In the embodiment in which the cover assembly includes a plurality of gas inlet ports, these ports are formed in the plenum member and are located to direct flow of the cooling gas between adjacent rows of reaction vials.

In embodiments where the outlet ports are formed within one of the sidewalls, the outlet ports are located to direct flow of the cooling gas between adjacent rows of reaction vials.

In another aspect, the invention provides a method of preparing a reaction mixture within a plurality of reaction vials. The method includes positioning the new cover assembly over the reaction vials in a block; providing a cooling gas from an external gas source to the internal cavity via the gas inlet to cool upper ends of the reaction vials; and heating the reaction vials to a predetermined reaction temperature by heating the base of the reaction block.

In certain embodiments, this method further includes positioning each of the plurality of reaction vials within a corresponding one of an array of first holes formed within a base of the reaction block.

A reaction mixture is added to each of the reaction vials prior to positioning the cover assembly over the reaction block.

As used in this method, the base can be formed of a first material having a first thermal conductivity characteristic and a spacer that includes an array of second holes located in a pattern corresponding to the array of first holes can be formed of a second material having a second thermal conductivity characteristic less than the first thermal conductivity characteristic.

In this method, the spacer can be a separate member and can be positioned between the base and cover prior to providing the reaction mixture within each of the reaction receptacles.

The reaction block allows reflux condensation to be performed independently within a large number of individual reaction vials or other receptacles, all of which are supported within the same reaction block. Different reaction mixtures can therefore be dispensed within the individual reaction receptacles and processed simultaneously. Thus, throughput in synthesizing reaction mixtures is increased.

The reaction block also provides a relatively simple, easily manufactured and assembled apparatus for performing reflux condensation reactions. The cover provides a single, open (i.e., no obstructing channel members) internal cavity through which the cooling gas is provided, e.g., through a single inlet.

Although methods and materials of the invention similar or equivalent to those described herein can be used in the practice or testing of the present invention, suitable methods and materials are described below.

Other features and advantages will be apparent from the following detailed description and drawings, and from the claims.

DETAILED DESCRIPTION

Figure 1:
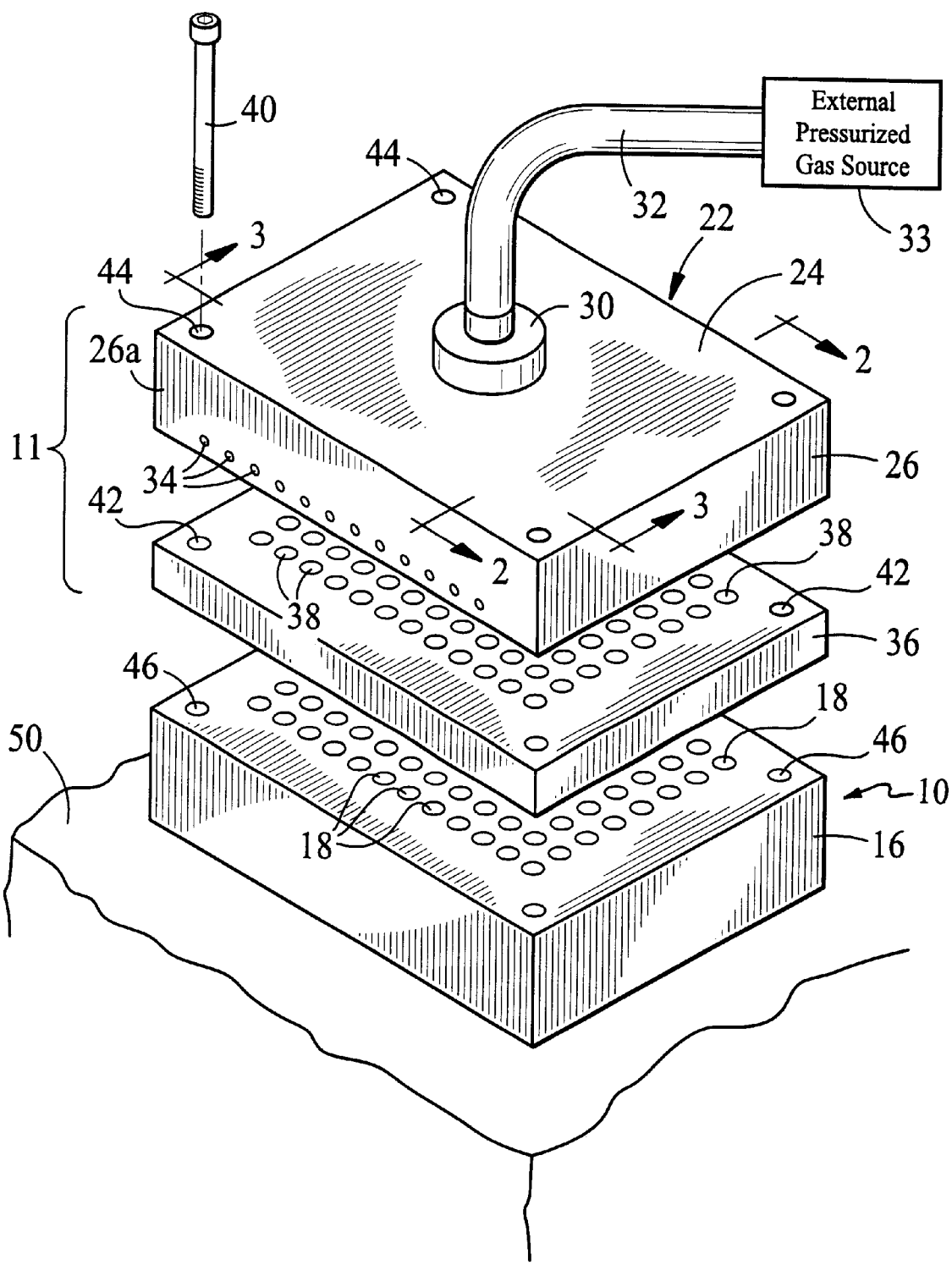
FIG. 1 is an exploded perspective view of a reaction block and cover assembly in accordance with the invention.
Figure 2:
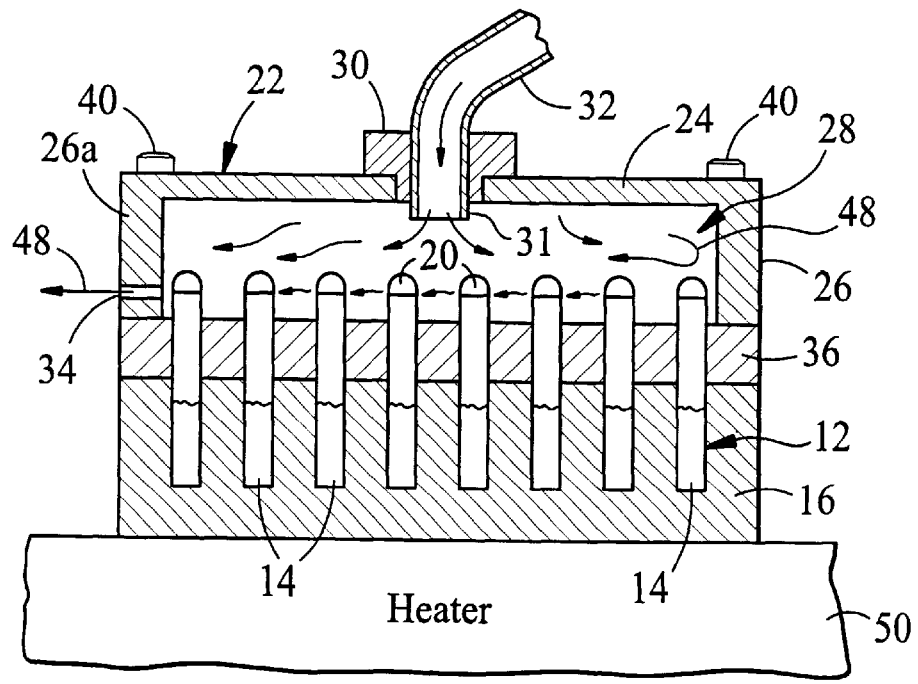
FIG. 2 is a cross-sectional side view of the reaction block and cover assembly along line 2—2 in FIG. 1.
Figure 3:
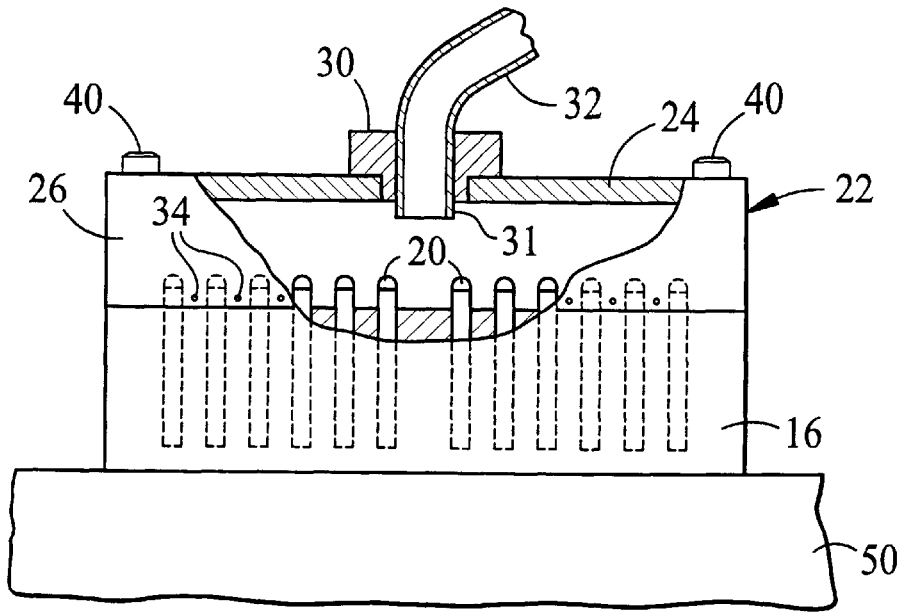
FIG. 3 is a side view, partially in cross section, of the reaction block and cover assembly along line 3—3 in FIG. 1.

Referring to FIGS. 1–3, a reaction block 10 supports an array of reaction vials 12 (FIG. 2) within which individual reflux condensation reactions are to be carried out. Each vial contains a reagent, which can be a solid, e.g., a powder, or a liquid. If a powder, a liquid is typically added to carry out a chemical action. For example, a reagent solution or mixture 14 can be formed. As will be discussed in greater detail below, many chemical reactions require heat to proceed.

Reaction block 10 includes a base 16 having a two-dimensional array of support holes 18 sized to receive reaction vials 12 containing reagent solution 14. The reaction block can accommodate a relatively large number of reaction vials. In the embodiment shown, 96 holes are provided in base 16. Other arrangements and numbers of holes (e.g., 384 holes) can be provided to suit particular needs. After the reagent solution is dispensed within vials 12, a cap may be placed over the open end of the vials to avoid possible contamination of the solution (or vapor products of the solution), thereby ensuring the integrity of the solution. In general, and in many applications, caps are not required to seal the vials if the reflux condensation process is carried out properly. Base 16 is preferably fabricated from a metal or other material having a relatively high thermal conductivity characteristic and capable of being heated to reaction temperatures of reagent solutions 14. For example, the base can be machined from 6061 aluminum and then anodized to provide corrosion protection. Other metals including copper and brass can be used to fabricate base 16. Support holes 18 are sufficiently deep to support reaction vials 12 at their lower ends while being sufficiently shallow to allow their upper ends to extend above the upper surface of base 16. By upper ends it is meant those ends excluding the lower ends received within the holes of base 16. The lower ends of reaction vials 12 are in intimate contact with base 16 when seated within support holes 18. Thus, when base 16 is heated, as will be discussed below, heat is efficiently and effectively transferred to the vials.

A cover assembly 11 includes a cover 22 positioned over base 16 of reaction block 10 and is in the form of a box-like enclosure having a top wall 24 and four sidewalls 26 which together define an internal volume 28 (FIG. 2) surrounding the upper ends of vials 12. In this embodiment, top wall 24 of cover 22 is spaced from the upper ends of the vials to provide an open area for the cooling gas to circulate. Alternatively, in other embodiments, top wall 24 may contact the upper ends of the vials, thereby securing them in place.

At least one inlet fixture 30 is positioned within a hole 31 (FIG. 2) formed in top wall 24 and is configured to be attached to a hose 32 connected to a fluid, such as a pressurized gas source 33. In many applications, cooling air is provided from gas source 33, e.g., a standardized pressurized air source at room temperature found in many laboratories which has the advantage of being readily available and inexpensive. However, in other applications, the pressurized gas source can be a specialized gas source that provides other gases or fluids, at room temperatures or at some predetermined cooling temperature. Cover 22 also includes exit openings 34 formed in one of the four sidewalls 26 so that with the cover positioned over base 16, the exit openings are between adjacent rows of vials 12.

An insulating spacer 36 having an array of thru holes 38 can be optionally placed between base 16 and cover 22. Spacer 36 can have a thickness, in this embodiment, of about 0.25 inches and can be formed of a thermally insulative material (e.g., polypropylene, polyethylene, teflon, or other inert material) capable of withstanding varying temperatures and chemical environments. Spacer 36 serves as a thermal isolating barrier between the upper and lower ends of vials 12, and between base 16 and cover 22.

Base 16, spacer 36, and cover 22 can be fastened together, for example, using screws 40 (only one being shown in FIG. 1), each of which extends through respective holes 42, 44 in the spacer and the cover, respectively, and received within threaded holes 46 of base 16. Alternative fastening approaches, including clamps, pins, etc., can be used as well.

In use, reaction vials 12 are placed within support holes 18 of base 16 with spacer 36 positioned thereon. The reaction solution 14 is dispensed into each vial 12, for example, using a syringe and needle which can be manipulated manually or, preferably, using an automated robotic system. Alternatively, the vials can be preloaded with a reagent or solvent before insertion into the base. Cover 22 is placed over spacer 36 and fastened to base 16 through spacer 36 using screws 40.

Hose 32 is connected to inlet fixture 30 and pressurized cooling gas (designated by arrows 48, e.g., at room temperature or lower, depending on the particular reaction) is directed into internal volume 28 of cover 22 to cool the upper ends of vials 12. Internal volume 28 of cover 22 is open and clear of obstructions. Thus, the upper ends of the array of vials form flow channels between the vials through which the pressurized gas 48 passes before exiting cover 22 via exit openings 34. Exit openings 34 are shown here along a single sidewall 26a of cover 22 so that gas 48 which enters internal volume 28 and is initially directed away from sidewalls within which exit openings 34 are formed, strikes the sidewalls 26 and is redirected back into the inner volume to be recirculated before eventually exiting through exit openings 34.

The reaction vials 12 are then heated, e.g., by placing the reaction block 10 on a heating block 50 or other heating device, to a temperature required by a particular reagent solution 14. Alternatively, base 16 can include electrical resistance heaters or other means of heating, so that base 16 can be heated independently and without the need for additional parts such as a heating block. Vapors released during reaction of the reagent solution rise to the upper end of vials 12, are cooled by the circulating gas in internal volume 28 and condensed on the inner sidewalls of the vials. The condensate then flows back to the lower end of vials 12 due to gravity. Thus, reaction block 10 enables a reflux condensation to occur during reaction of the reagent solution.

Figure 4:
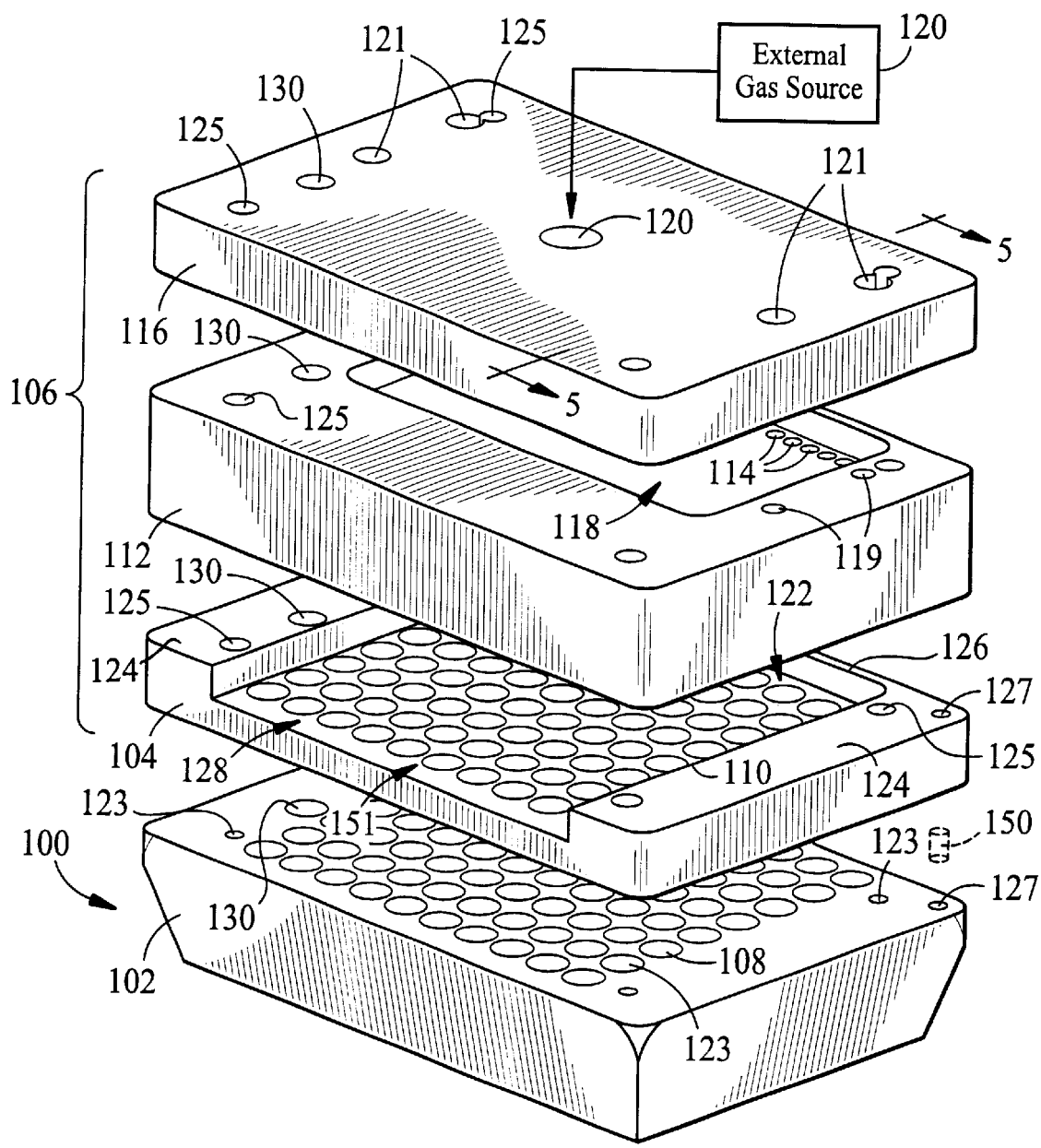
FIG. 4 is an exploded perspective view of an alternative embodiment of a reaction block and cover assembly.
Figure 5:
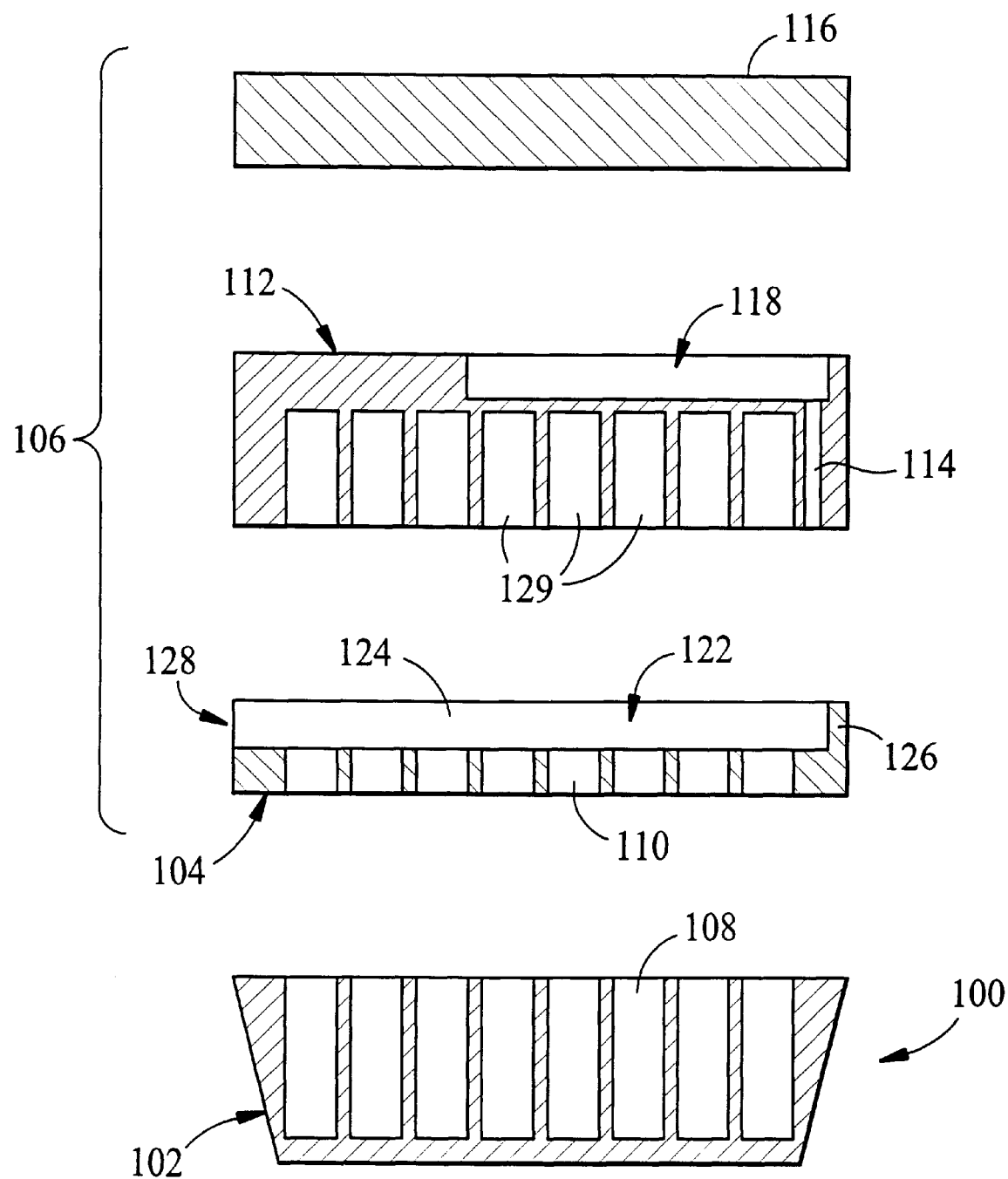
FIG. 5 is a cross-sectional side view of the reaction block and cover assembly along line 5—5 in FIG. 4.

Referring to FIGS. 4 and 5, in another embodiment of the invention, a cover assembly 106 is positioned over a base 102 having an array of holes 108 for supporting reaction vials. Cover assembly 106 includes an insulating spacer 104, a plenum member 112 having a series of gas ports 114 extending therethrough, and a top 116. When top 116 is placed over plenum member 112 a plenum chamber 118 is provided therebetween. As was the case with spacer 36 of reaction block 10, spacer 104 is formed of a thermally insulative material such as polypropylene, and includes an array of holes 110 which surround a central portion of the reaction vials. As shown most clearly in FIG. 5, the underside of plenum member 112 includes an array of holes 129 for capturing the upper ends of the reaction vials.

Threaded hole 119 of plenum member 112 receives fastening screws (not shown) which extend through holes 121 of top 116 to provide a tight seal around the periphery of plenum chamber 118. Base 102 similarly includes holes 123 some of which receive fastening screws or alignment pins (neither shown) extending through holes 125 of cover assembly 106. Base 102 and spacer 104 also include a visual hole, serving as a key 127 to ensure proper registration of cover assembly 106 to the base. Alternatively, a pin, 150, can be inserted into hole 127 of plate 102 and pass through holes 127 of spacer 104 and into hole 127 of plenum member 112 to provide alignment. A thru-hole 130, used to receive a temperature measuring device (e.g., a thermometer) extends through top 116, plenum member 112, spacer 104 and into base 102.

In operation, a cooling gas is provided within plenum chamber 118 from an external gas source 121 through a gas inlet 120 of top 116. The pressurized gas exits plenum chamber 118 through gas ports 114 and into a cooling chamber 122 formed by the interface between the bottom surface of plenum member 112 and an outer wall of spacer 104 consisting of sidewalls 124, an endwall 126 and surface 151. Pressurized gas entering cooling chamber 122 strikes surface 151 of spacer 104 and endwall 126 and is then redirected toward an opening 128 formed at an end of spacer 104 opposite endwall 126. As was the case with exit openings 34 of reaction block 10, gas ports 114 are sized to efficiently distribute the pressurized gas into cooling chamber 122.

Figure 6:
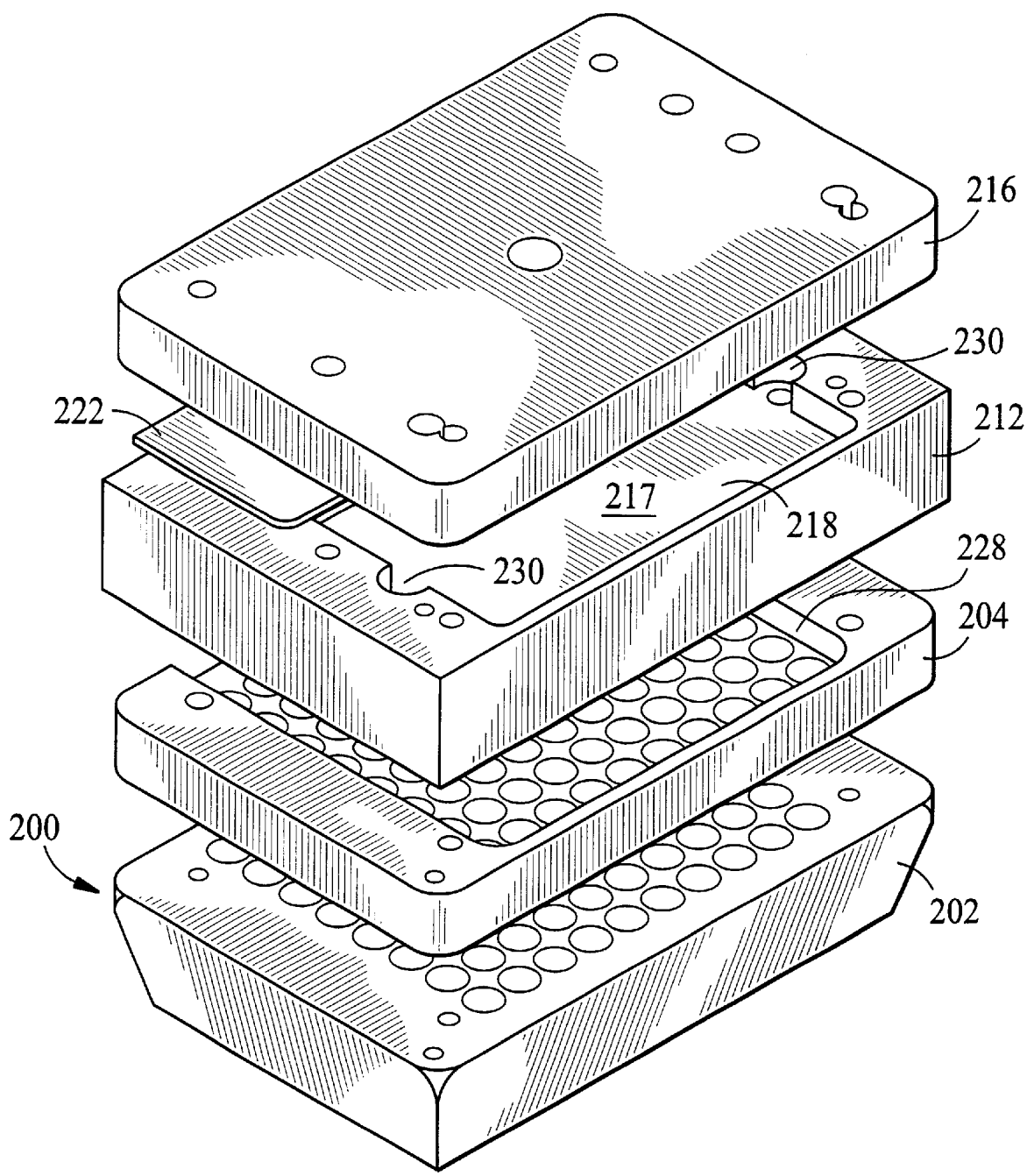
FIG. 6 is an exploded perspective view of another alternative embodiment of a reaction block and cover assembly.
Figure 8:
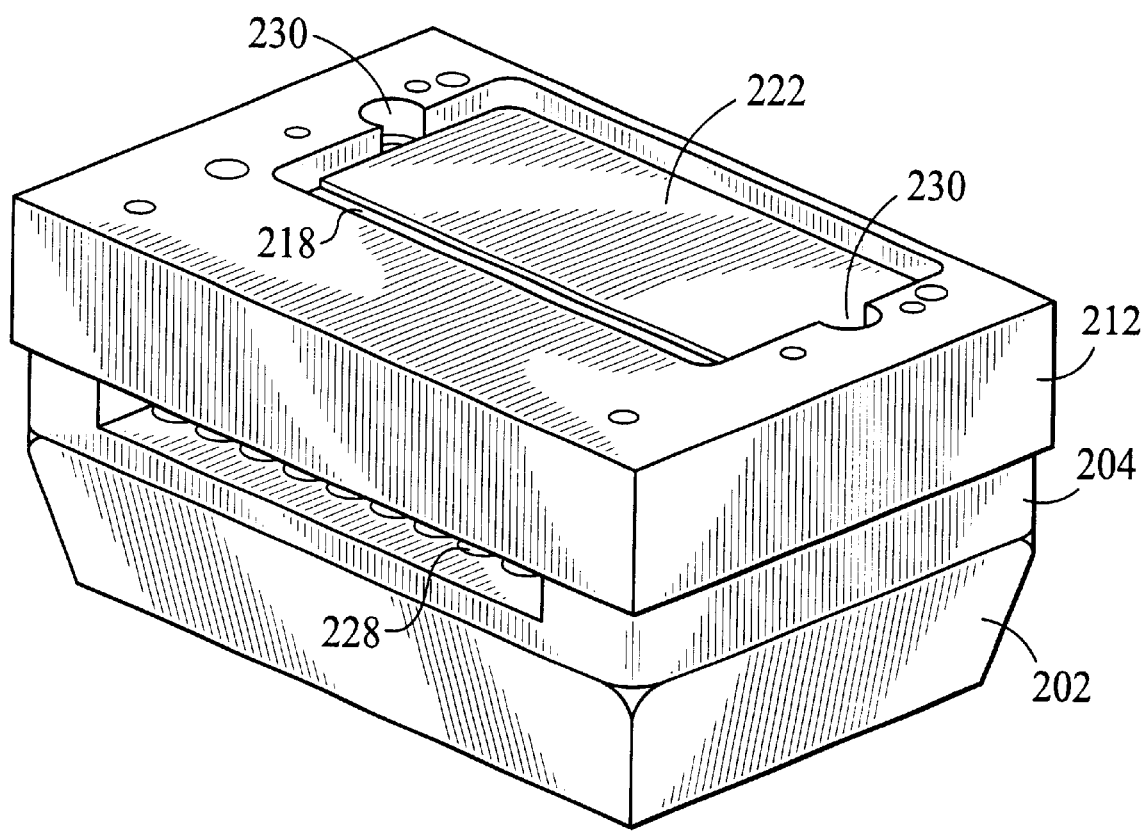
FIG. 8 is a perspective view of the embodiment of the reaction block and cover assembly (without top cover) of FIG. 6.

Referring to FIGS. 6 and 8, an alternative embodiment of a reaction block 200 includes a mechanism for controlling the volume of air flow used to cool the vials.

In this embodiment, a base 202, spacer 204, plenum member 212, and cover 216 are constructed similarly to base 102, spacer 104, plenum member 112, and cover 116 of reaction block 100, respectively. Plenum member 212, however, does not include gas ports. Instead, plenum member 212 together with cover 216 defines a plenum chamber 218 having a slot 220 formed along a side wall 221 of the chamber. Disposed on bottom surface 217 of plenum chamber 218 is a relatively thin sliding vane 222 which is positioned to cover no part or some portion of slot 220, thereby controlling the velocity of the cooling gas flowing into a cooling chamber 228 of spacer 204. As shown most clearly in FIG. 8, plenum member 212 includes a pair of threaded holes 230 for receiving lock down screws (not shown) to secure vane 222 in place once the desired position of the sliding vane is determined.

By providing a mechanism which controls the size of the opening into the slot, greater flexibility is provided to the user. Specifically, by varying the size of the opening into slot 220, the velocity of the cooling gas is varied, thereby varying the cooling rate of the gas. Among other advantages, the number and size of the vials accommodated in the base can be varied simply by substituting a different base. As a result, a wider variety of reflux condensation processes can be performed with a single reaction block system having, for example, interchangeable bases.

Figure 7:
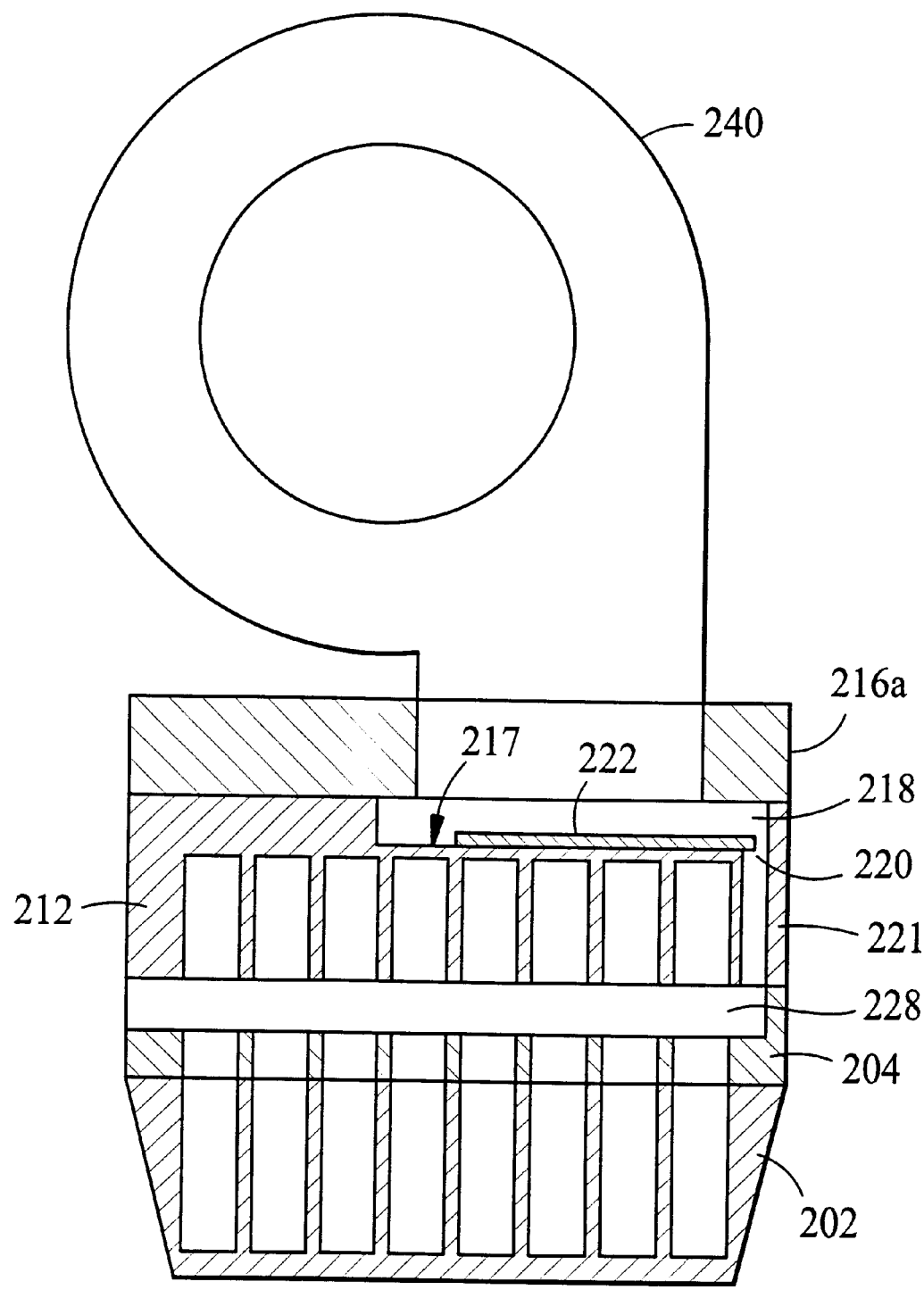
FIG. 7 is a cross-sectional side view of a reaction block and cover assembly similar to that in FIG. 6, including a fan.

It is to be appreciated that the invention encompasses the use of sources other than pressurized cooling gas. Referring to FIG. 7, for example, reaction block 200 includes a cover 216a configured to receive a fan 240 (e.g., muffin fan) for cooling the vials. Fan 240 is a single speed fan with the velocity of the air controlled by moving vane 222. Alternatively, a variable speed fan may be used, for example with the embodiments of FIGS. 1–4 without moveable vanes.

Reaction blocks 10, 100, and 200 were described above as being used with separate and removable spacers 36, 104, 204, respectively. However, in certain applications, use of a spacer to thermally isolate the upper and lower ends of the vials may not be necessary, and thus the spacer can be removed. Alternatively, the spacer can be permanently affixed as part of the base 12 or cover to form an integral unit.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A cover assembly configured to be disposed over a reaction block which during operation supports a plurality of reaction vials, the cover assembly comprising:
   a cover housing including:
      a gas inlet adapted to receive a cooling gas from an external source;
   the cover housing defining, in part, an internal cavity into which the reaction vials extend during operation;
   a plenum member defining, in part, a plenum chamber and having a gas port extending therethrough, the plenum member being positioned between the gas inlet and the internal cavity such that the cooling gas flows from the gas inlet and through the gas port to cool upper ends of the reaction vials;
   a movable vane disposed within the plenum chamber and configured to be positioned and secured over a portion of the gas port; and
   an outlet configured to allow the cooling gas to exit the internal cavity after cooling the upper ends of the reaction vials.

2. The cover assembly of claim 1 wherein the
   a plenum member has an upper surface, and a bottom surface;
   the cover assembly comprising:
      a top cover disposed over the plenum member and having a bottom surface which together with the upper surface of the plenum member define the plenum chamber, the gas inlet being provided within the top cover; and
      a spacer positioned between the plenum member and the reaction block, the spacer having an upper surface which together with the bottom surface of the plenum member defines the internal cavity and the gas outlet.

3. A reaction block comprising:
   the cover assembly recited in claim 2; and
   a base including an array of first holes formed therein, each of the first holes sized and configured to receive a lower end of a reaction vial.

4. The reaction block of claim 3, wherein the spacer includes an array of second holes located in a pattern corresponding to the array of first holes.

5. The reaction block of claim 3, wherein the array of first holes defines a pattern of rows and columns.

6. The reaction block of claim 3, wherein the base is formed of a first material having a first thermal conductivity characteristic and the spacer is formed of a thermally insulative material having a second thermal conductivity characteristic less than the first thermal conductivity characteristic.

7. A cover assembly configured to be disposed over a reaction block which during operation supports a plurality of reaction vials, the cover assembly comprising:
   a cover housing defining in part an internal cavity into which the reaction vials extend during operation, the cover housing including:
      a gas inlet adapted to receive a cooling gas from an external source;
   a plenum member having an upper surface, a bottom surface, and a plurality of gas ports, positioned between the gas inlet and the internal cavity and through which the cooling gas from the gas inlet flows to cool upper ends of the reaction vials; and
   an outlet configured to allow the cooling gas to exit the internal cavity after cooling upper ends of the reaction vials.

8. The cover assembly of claim 7, wherein the cover housing includes:
   a top cover disposed over the plenum member and having a bottom surface which together with the upper surface of the plenum member define the plenum chamber, the gas inlet provided within the top cover; and
   a spacer positioned between the plenum member and the reaction block, the spacer having an upper surface which together with the bottom surface of the plenum member defines the internal cavity and the outlet.

9. A reaction block comprising:
   the cover assembly recited in claim 8; and
   a base including an array of first holes formed therein, each of the first holes sized and configured to receive a lower end of a reaction vial.

10. The reaction block of claim 9, wherein the spacer includes an array of second holes located in a pattern corresponding to the array of first holes.

11. The reaction block of claim 9, wherein the array of first holes defines a pattern of rows and columns.

12. The reaction block of claim 11, wherein the gas inlet ports formed in the plenum member are located to direct flow of the cooling gas between adjacent rows of reaction vials.

13. The reaction block of claim 9, wherein the base is formed of a first material having a first thermal conductivity characteristic and the spacer is formed of a thermally insulative material having a second thermal conductivity-characteristic less than the first thermal conductivity characteristic.

14. A reaction block which during operation supports a plurality of reaction vials, the reaction block comprising:
   a base including an array of first holes formed therein, each of the first holes sized and configured to receive a lower end of a reaction vial, the base being formed of a first material having a first thermal conductivity characteristic; and
   a cover assembly including:
      a gas inlet adapted to receive a pressurized cooling gas from an external source;
      a top wall and a plurality of sidewalls which together define, in part, an internal cavity adapted to receive upper ends of each reaction vial during operation; and
      a plurality of outlet ports formed within at least one of the sidewalls to allow the cooling gas to exit the internal cavity after cooling the upper ends of each reaction vial; and
      an insulative spacer positioned over the base, the insulative spacer including an array of second holes located in a pattern corresponding to the array of first holes and formed of a second material having a second thermal conductivity characteristic less than the first thermal conductivity characteristic.

15. The cover assembly of claim 14, wherein the outlet ports formed within one of the sidewalls are located to direct flow of the cooling gas between adjacent rows of reaction vials.

16. The reaction block of claim 14, wherein the array of first holes defines a pattern of rows and columns.

17. A cover assembly configured to be disposed over a reaction block which during operation supports a plurality of reaction vials, the cover assembly comprising:
   a cover housing including:
      a gas inlet adapted to receive a cooling gas from an external source;

the cover housing defining, in part, an internal cavity into which the reaction vials extend during operation;

a plenum member defining a plenum chamber and having a gas port extending therethrough, the plenum member being positioned between the gas inlet and the internal cavity such that the cooling gas flows from the gas inlet and through the gas port to cool upper ends of the reaction vials; and an outlet configured to allow the cooling gas to exit the internal cavity after cooling the upper ends of the reaction vials.

18. The cover assembly of claim 17 wherein the a plenum member has an upper surface, and a bottom surface;

the cover assembly further comprising:

a top cover disposed over the plenum member and having a bottom surface which together with the upper surface of the plenum member define the plenum chamber, the gas inlet being provided within the top cover; and a spacer positioned between the plenum member and the reaction block, the spacer having an upper surface which together with the bottom surface of the plenum member defines the internal cavity and the gas outlet.

19. A reaction block comprising:

the cover assembly recited in claim 18; and a base including an array of first holes formed therein, each of the first holes sized and configured to receive a lower end of a reaction vial.

20. The reaction block of claim 19, wherein the spacer includes an array of second holes located in a pattern corresponding to the array of first holes.

21. The reaction block of claim 19, wherein the array of first holes defines a pattern of rows and columns.

22. The reaction block of claim 19, wherein the base is formed of a first material having a first thermal conductivity characteristic and the spacer is formed of a thermally insulative.

23. A method of preparing a reaction mixture within a plurality of reaction vials in a reaction block, the method comprising:

positioning the cover assembly of claim 17 over the reaction vials in the block;

providing a cooling gas from an external gas source to the internal cavity via the gas inlet to cool upper ends of the reaction vials; and heating the reaction vials to a predetermined reaction temperature by heating the base.

24. The method of claim 23, further comprising positioning each of the plurality of reaction vials within one of an array of first holes formed within a base of the reaction block.

25. The method of claim 24, further comprising adding a reaction mixture to each of the reaction vials prior to positioning the cover assembly over the reaction block.

26. The method of claim 23, wherein the plenum member has an upper surface, and a bottom surface; the cover assembly comprising:

a top cover disposed over the plenum member and having a bottom surface which together with the upper surface of the plenum member define the plenum chamber, the gas inlet provided within the top cover; and a spacer positioned between the plenum member and the reaction block, the spacer having an upper surface which together with the bottom surface of the plenum member defines the internal cavity and the gas outlet, and the base is formed of a first material having a first thermal conductivity characteristic and the spacer includes an array of second holes located in a pattern corresponding to the array of first holes, the spacer formed of a second material having a second thermal conductivity characteristic less than the first thermal conductivity characteristic.

27. The method of claim 26, wherein the spacer is a separate member and is positioned between the base and cover prior to providing the reaction mixture within each of the reaction receptacles.

* * * * *

UNITED STATES PATENT AND TRADEMARK OFFICE
CERTIFICATE OF CORRECTION

| | | |
|---|---|---|
| PATENT NO. | : 6,238,627 B1 | Page 1 of 1 |
| DATED | : May 29, 2001 | |
| INVENTOR(S) | : David Craig McGowan, Erik T. Mankarios, Edward M. Manley, Christopher C. Werner, and Meinolf Lange | |

It is certified that error appears in the above-identified patent and that said Letters Patent is hereby corrected as shown below:

Please replace the list of inventors with the following paragraph:
-- David Craig McGowan, Arlington; Erik T. Mankarios, Needham; Edward M. Manley, Medford; Christopher C. Werner, Bellingham; and Meinolf Lange, Woburn, all of MA (US) --

Signed and Sealed this

Twenty-eighth Day of June, 2005

JON W. DUDAS
*Director of the United States Patent and Trademark Office*